United States Patent
Leger et al.

(10) Patent No.: US 6,693,711 B1
(45) Date of Patent: Feb. 17, 2004

(54) ELLIPSOMETER USING RADIAL SYMMETRY

(75) Inventors: James R. Leger, Plymouth, MN (US); Qiwen Zhan, Lauderdale, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/691,346

(22) Filed: Oct. 18, 2000

Related U.S. Application Data
(60) Provisional application No. 60/204,238, filed on May 15, 2000.

(51) Int. Cl.⁷ .................................................. G01J 4/00
(52) U.S. Cl. ...................................... 356/369; 356/364
(58) Field of Search ................................ 356/368, 381, 356/382, 364, 365, 366, 367, 370; 250/372, 225

(56) References Cited

U.S. PATENT DOCUMENTS

| | | |
|---|---|---|
| 5,022,743 A | 6/1991 | Kino et al. |
| 5,042,951 A | 8/1991 | Gold et al. |
| 5,133,601 A | 7/1992 | Cohen et al. |
| 5,159,412 A | 10/1992 | Willenborg et al. |
| 5,181,080 A | 1/1993 | Fanton et al. |
| 5,204,734 A | 4/1993 | Cohen et al. |
| 5,359,622 A | 10/1994 | Shih |
| 5,486,701 A * | 1/1996 | Norton et al. ............... 250/372 |
| 5,521,705 A * | 5/1996 | Oldenbourg et al. ........ 356/368 |
| 5,602,643 A | 2/1997 | Barrett |
| 5,602,820 A | 2/1997 | Wickramasinghe et al. |
| 5,754,296 A | 5/1998 | Law |
| 5,910,841 A | 6/1999 | Masao |
| 5,939,709 A | 8/1999 | Ghislain et al. |
| 5,963,326 A | 10/1999 | Masao |
| 6,008,892 A | 12/1999 | Kain et al. |
| 6,177,990 B1 | 1/2001 | Kain et al. |
| 6,404,544 B1 | 6/2002 | Kuhn |

OTHER PUBLICATIONS

Albersodorfer et al., "High resolution imaging microellipsometry of soft surfaces at 3μm lateral and 5 Å normal resolution", *Appl. Phys. Lett.*, 72(23):2930–2932 (1998).

Azzam et al., "Ellipsometry and Polarized Light", Amsterdam, North Holland Physiscs Publishing (1988).

Beam Profile Ellipsometry (BPE). Therma-wave [retrieved on Jan. 15, 2000]. Retrieved from the Internet: <URL: http://www.thermawave.com/technology/bpe.htm>, 1 page.

Chou et al., "Subwavelength amorphous silicon transmission gratings and applications in polarizers and waveplates", *Appl. Phys. Lett.*, 67(6):742–744 (1995).

Chou et al., "Dynamic imaging microellipslmetry: theory, system design, and feasibility demonstration", *Applied Optics*, 27(22):4664–4671 (1988).

Erman et al., "Spatially resolved ellipsometry", *J. Appl. Phys.*, 60(3):859–873 (1986).

Jin et al., "Imaging ellipsometry revisited: Developments for visualization of thin transparent layers on silicon substrates", *Rev. Sci. Instrum.*, 67(8):2930–2935 (1996).

(List continued on next page.)

Primary Examiner—Michael P. Stafira
(74) Attorney, Agent, or Firm—Mueting, Raasch & Gebhardt, P.A.

(57) ABSTRACT

An ellipsometer and ellipsometry method uses radial symmetry. For example, circularly polarized light may be focused to a spot on a sample using an objective lens and reflected therefrom. A radially symmetric ellipsometric signal based on the reflected light and representative of at least one characteristic of the sample may be attained using a radially symmetric analyzer apparatus, e.g., a pure Polarization rotator such as two half wave plates and a radially symmetric analyzer such as a birefringent lens.

34 Claims, 12 Drawing Sheets

OTHER PUBLICATIONS

I–Elli2000 Imaging Ellipsometer. Nano–film Technologie [retrieved on Jan. 15, 2001]. Retrieved from Internet: <URL: http:www.nanofilm.ed/html/elli2000/body_i–elli2000.html>, 16 pages.

Imaging Ellipsometer. Beaglehole Instruments [retrieved on Jan. 15, 2001]. Retrieved from Internet: <URL: http://www.beaglehole.com/imelli/im–main.html>, 9 pages.

Karlsson, "Detector and Data Acquistion System for an Imaging Ellipsometer", IEEE Instrumentation and Measurement Technology Conference, St. Paul, Minnesota, USA, May 18–21, 1998, 1:679–382 (1998).

Leng et al., "Characterization of titanium nitride (TiN) films on various substrates using spectrophotometry, beam ellipsometry", *Thin Solid Films, 313–341*: 308–313 (1998).

Leng et al., "Combined beam profile reflctrometry, beam ellipsometry and ultraviolet–visible spectrophotometry for the characterization of ultathin oxide–nitride–oxide films on silicon", *J. Vac. Sci. Techn., A17*(2):380–384 (1999).

Liu et al., "Image scanning ellipsometry for measuring nonuniform film thickness profiles", *Applied Optics, 33*(7):1223–1229 (1994).

Logofatu et al., "Identity of the cross–reflection coefficients for symmetric surface–relief gratings", *J. Opt. Soc. Am. A, 15*(5):1108–1114 (1999).

Mansfield et al., "Solid immersion microscope", *Appl. Phys. Lett., 57*(24):2615–2616 (1990).

Mansuripur, "Certain computational aspects of vector diffraction problems", *J. Opt. Soc. Am. A, 6*(5):786–805 (1989).

Mansuripur, "Distribution of light at and near the focus of high–numerical–aperture objectives", *J. Opt. Soc. Am. A, 3*(12):2086–2093 (1986).

Nordin et al., "Broadband form birefringent quarter–wave plate for the midinfrared wavelength region", *Optics Express, 5*(8):163–168 (1999).

Rosencwaig et al., "Beam profile reflectometry: a new technique for dielectric film measurements", *Appl. Phys. Lett., 60*(11):1301–1303 (1992).

See et al., "Scanning optical microellipsometer for pure surface profiling", *Applied Optics, 35*(34):6663–6668 (1996).

Spesivtsev et al., "Automatic Scanning Microellipsometer", *Optoelectr., Instrum. and Data Process., 1*:90–94 (1997).

Tompkins et al., "Spectroscopic Ellipsometry and Refectoletry", N.Y., John Wiley & Sons, Inc. (1999).

Ye, "Non mechanical half–wave plate polorization rotator", *Optik, 101*(2):77–79 (1995).

Absolute Ellipsometry (AE). Therma–Wave Measurement Technologies [retrieved from the Internet on Feb. 11, 2003]. http://thermawave.com/technology/ae.htm., 1 page.

Ashkin, "History of Optical Trapping and Manipulation of Small–Neutral Particle, Atoms and Molecules," *IEEE Journal on Selected Topics in Quantum Electronics*, 2000; 6(6):841–856.

Beijerbergen et al., "Helical–wavefront laser beams produced with a spiral phaseplate," *Optics Comm.*, 1994; 112:321–327.

Berger et al., "Resolution in surface plasmon microscopy," *Rev. Sci. Instrum.*, 1994; 65:2829–2836.

Biss et al., "Cylindrical vector beam focusing through a dielectric interface," *Optics Express*, 2001; 9(10):490–497.

Courtial et al., "Rotational Frequency Shift of a Light Beam," *Phys. Rev. Lett.*, 1998; 81(22):4828–4830.

DUV Spectroscopic Ellipsometry (SE). Therma–Wave Measurement Technologies [retrieved from the Internet on Feb. 11, 2003]. http://www.thermawave.com/technology/duvse.htm. 1 page.

Goodman, Introduction to Fourier Optics, 2d ed., New York, 1996; cover page, title page and table of contents, 8 pgs.

Gu (editor), *Advanced Optical Imaging Theory*, Springer Series in Optical Sciences, New York, 2000, 8 pgs.

Hafizi et al., "Laser–driven acceleration with Bessel beams," *Phys. Rev. E*, 1997; 55(3):3539–3545.

Harada et al., "Radiation forces on a dielectric sphere in the Rayleigh scattering regime" *Optics Comm.*, 1996; 124:529–541.

He et al., "Direct Observation of Transfer of Angular Momentum to Absorptive Particles from a Laser Beam with a Phase Singularity," *Phys. Rev. Lett.*, 1995; 75(5):826–829.

Hsieh et al., "Image contrast in polarization microscopy of magneto–optical disk data–storage media through birefringent plastic substrates," *Appl. Opt.*, 1997; 36(20):4839–4852.

Kano et al., "Excitation of surface–plasmon polaritons by a focused laser beam," *J. Opt. Soc., Am. B*, 1998; 15(4):1381–1386.

Kuga et al., "Novel Optical Trap of Atoms with a Doughnut Beam," *Phys. Rev. Lett.*, 1997; 78(25):4713–4716.

Liu et al., "Vector diffraction from subwavelength optical disk structures: two–dimensional modeling of near–field profiles, far–field intensities, and detector signals from a DVD," *Appl. Opt.*, 1999; 38(17):3787–3797.

Mansuripur, *The Physical Principles of Magneto–Optical Recording*, Cambridge, Mass. 1995; cover page, title page, table of contents, 10 pgs.

Minhas et al., "Ellipsometric scatterometry for the metrology of sub–0.1–$\mu$m–linewidth structures," *Appl. Opt.*, 1998; 37(22):5112–5115.

Mirotznik et al., "Three–Dimensional Vector–Based Analysis of Sub–Wavelength Diffractive Optical Elements Using the Finite–Difference Time–Domain (FDTD) Method," *Diffractive Optics and Micro–Optics, 10*; 1998, OSA Technical Digest Series (Optical Society of America, Washington, D.C.); 91–93.

Mirotznik et al., "A hybrid finite element–boundary element method for the analysis of diffractive elements," *J. Mod. Opt.*, 1996; 43(7):1309–1321.

Moharam et al., "Diffraction analysis of dielectric surface–relief gratings," *J. Opt. Soc. Am.*, 1982; 72(10):1385–1392.

Moharam et al., "Formulation for stable and efficient implementation of the rigorous coupled–wave analysis of binary gratings," *J. Opt. Soc. Am. A*, 1995; 12(5):1068–1076.

Moharam et al., "Stable implementation of the rigorous coupled–wave analysis for surface–relief gratings: enhanced transmittance matrix approach," *J. Opt. Soc. Am. A*, 1995; 12(5):1077–1086.

Niziev et al., "Influence of beam polarization on laser cutting efficiency," *J. Phys. D*, 1999; 32:1455–1461.

Oron et al., "Efficient formation of pure helical laser beams," *Optics Comm.*, 2000; 182:205–208.

Oron et al., "The formation of laser beams with pure azimuthal or radial polarization," *Appl. Phys. Lett.*, 2000; 77(21):3322–3324.

Otaki et al., "Polarization Effect on Signal from Optical ROM Using Solid Immersion Lens," *Jpn. J. Appl. Phys.*, 2000; 39:698–706.

Paesler et al., "Optical Tunneling Microscopes," *Near–Field Optics, Theory, Instrumentation, and Applications*, New York, New York, 1996, 143–161.

Prather et al., "Formulation and application of the finite–difference time–domain method for the analysis of axially symmetric diffractive optical elements," *J. Opt. Soc. Am. A*, 1999; 16(5):1131–1142.

Quabis et al., "The focus of light–theoretical calculation and experimental tomographic reconstruction," *Appl. Phys. B*, 2001; 72:109–113.

Raether, *Surface Plasmons on Smooth and Rough Surfaces and on Gratings*, Spinger–Verlag, Berlin, 1998, cover page, title page, table of contents, 4 pgs.

Richards et al., "Electromagnetic diffraction in optical systems II. Structure of the image field in an aplanatic system," *Proc. R. Soc. London Ser. A*, 1959; 253:358–379.

Rothenhäusler et al., "Surface–plasmon microscopy," *Nature*, 1998; 332:615–617.

Sato et al., "Optical trapping of microscopic metal particles," *Opt. Lett.*, 1994; 19(22):1807–1809.

Somekh et al., "Optical V(z) for high resolution 2π surface plasmon microscopy," *Opt. Lett.*, 2000; 25(11):823–825.

Stalder et al., "Linearly polarized light with axial symmetry generated by liquid–crystal polarization converters," *Opt. Lett.*, 1996; 21(23):1948–1950.

Taflove et al., *Computational Electrodynamics—The Finite–Difference Time–Domain Method*, Boston, Mass., 1995; cover page, title page, table of contents, 13 pgs.

Tominaga et al., "Local plasmon photonic transistor," *Appl. Phys. Lett.*, 2001; 78(17):2417–2419.

Tompkins, *A User's Guide to Ellipsometry*, Boston, Mass., 1993; cover page, title page, table of contents, 9 pgs.

Wang et al. "Measuring and modeling optical diffraction from subwavelength features," *J. Opt. Soc. Am. A*, 2001; 18(3):565–572.

Wolf, "Electromagnetic diffraction in optical systems I. An integral representation of the image field," *Proc. R. Soc. Ser. A*, 1959; 253:349–357.

Wu et al., "Realization of numerical aperture 2.0 using a gallium phosphide solid immersion lens," Applied Physics Letters, 1999; 75(26):4064–4066.

Youngworth et al., "Focusing of high numerical aperture cylindrical–vector beams," *Optics Express*, 2000; 7(2):77–87.

Zhan, "Novel Polarization Measurement and Manipulation Techniques for Nanometer Scale Applications," Thesis, University of Minnesota, Aug. 2002, 12 pgs.

Zhan, "Radiation forces on a dielectric sphere produced by highly focused cylindrical vector beams," *J. Opt. A: Pure Appl. Opt.*, 2003; 5:229–232.

Zhan et al., "Measurement of surface features beyond the diffraction limit using an imaging ellipsometer," *Optics Letters*, 2000; 27(10):821–823.

Zhan et al., "Imaging ellipsometry for high–spatial–resolution metrology," University of Minnesota, Minneapolis, MN, SPIE Proceedings, "Wave optics and VLSI photonic devices for information processing," 2001; 4435:65–76.

Zhan et al., "High–resolution imaging ellipsometer," *Applied Optics*, 2002;41(22):4443–4450.

Zhan et al., "Interferometric measurement of the geometric phase in space–variant polarization manipulations," *Optics Communications*, 2002; 213:241–245.

Zhan et al., "Focus shaping using cylindrical vector beams," *Optics Express*, 2002; 10(7):324–331.

Zhan et al., "Near–field nano–ellipsometer for ultrathin film characterization," *Journal of Microscopy*, 2003;210(Pt. 3):214–219.

* cited by examiner

ELLIPSOMETER USING RADIAL SYMMETRY

CROSS REFERENCE TO RELATED APPLICATION

The present application claims the benefit of U.S. Provisional Patent Application Ser. No. 60/204,238, filed May 15, 2000, and entitled "Ellipsometer Using Radial Symmetry."

FIELD OF THE INVENTION

The present invention relates generally to ellipsometry. More particularly, the present invention pertains to ellipsometric methods and apparatus using radial symmetry.

BACKGROUND OF THE INVENTION

Ellipsometry is an optical technique that uses polarized light to probe the properties of a sample. The most common application of ellipsometry is the analysis of very thin films. Through the analysis of the state of polarization of the light that interacts with the sample, ellipsometry can yield information about such films. For example, depending on what is already known about the sample, the technique can probe a range of properties including the layer thickness, morphology, or chemical composition.

Generally, optical ellipsometry can be defined as the measurement of the state of polarized light waves. An ellipsometer measures the changes in the polarization state of light when it interacts with a sample. The most common ellipsometer configuration is a reflection ellipsometer, although transmission ellipsometers are sometime used. If linearly polarized light of a known orientation is reflected or transmitted at oblique incidence from a sample surface resultant light becomes elliptically polarized. The shape and orientation of the ellipse depend on the angle of incidence, the direction of the polarization of the incident light, the wavelength of the incident light, and the Fresnel properties of the surface. The polarization of the light is measured for use in determining characteristics of the sample. For example, in one conventional null ellipsometer, the polarization of the reflected light can be measured with a quarter-wave plate followed by an analyzer. The orientation of the quarter-wave plate and the analyzer are varied until no light passes though the analyzer, i.e., a null is attained. From these orientations and the direction of polarization of the incident light, a description of the state of polarization of the light reflected from the surface can be calculated and sample properties deduced.

Two characteristics of ellipsometry make its use particularly attractive. First, it is a nondestructive technique, such that it is suitable for in situ observation. Second, the technique is extremely sensitive. For example, it can measure small changes of a film down to sub-monolayer of atoms or molecules. For these reasons, ellipsometry has been used in physics, chemistry, materials science, biology, metallurgical engineering, biomedical engineering, etc.

As mentioned above, one important application of ellipsometry is to study thin films, e.g., in the fabrication of integrated circuits. In the context of ellipsometry, a thin film is one that ranges from essentially zero thickness to several thousand Angstroms, although this range can be extended in many cases. The sensitivity of an ellipsometer is such that a change in film thickness of a few Angstroms can usually be detected. From the measurement of changes in the polarization state of light when it is reflected from a sample, an ellipsometer can measure the refractive index and the thickness of thin films, e.g., semi-transparent thin films. The ellipsometer relies on the fact that the reflection at a material interface changes the polarization of the incident light according to the index of refraction of the interface materials. In addition, the polarization and overall phase of the incident light is changed depending on the refractive index of the film material as well as its thickness.

Generally, for example, a conventional reflection ellipsometer apparatus, such as shown in FIG. 1, includes a polarizer arm 12 and an analyzer arm 14. The polarizer arm 12 includes a light source 15 such as a laser (commonly a 632.8 nm helium/neon laser or a 650–850 nm semiconductor diode laser) and a polarizer 16 which provides a state of polarization for the incident light 18. The polarization of the incident light may vary from linearly polarized light to elliptically polarized light to circularly polarized light. The incident light 18 is reflected off the sample 10 or layer of interest and then analyzed with the analyzer arm 14 of the ellipsometer apparatus. The polarizer arm 12 of the ellipsometer apparatus produces the polarized light 18 and orients the incident light 18 at an angle 13 with respect to a sample plane 11 of the sample 10 to be analyzed, e.g., at some angle such as 20 degrees with respect to the sample plane 11 or 70 degrees with respect to the sample normal.

The reflected light 20 is examined by components of the analyzer arm 14, e.g., components that are also oriented at the same fixed angle with respect to the sample plane 11 of the sample 10. For example, the analyzer arm 14 may include a quarter wave plate 22, an analyzer 24 (e.g., a polarizer generally crossed with the polarizer 16 of the polarizer arm 12), and a detector 26. To measure the polarization of the reflected light 20, the operator may change the angle of one or more of the polarizer 16, analyzer 24, or quarter wave plate 22 until a minimal signal is detected. For example, the minimum signal is detected if the light 20 reflected by the sample 10 is linearly polarized, while the analyzer 24 is set so that only light with a polarization which is perpendicular to the incoming polarization is allowed to pass. The angle of the analyzer 24 is therefore related to the direction of polarization of the reflected light 20 if the minimum condition is satisfied. The instrument is "tuned" to this null (e.g., generally automatically under computer control), and the positions of the polarizer 16, the analyzer 24, and the incident angle 13 of the light relative to the sample plane 11 of the sample 10 are used to calculate the fundamental quantities of ellipsometry: the so called Psi, delta ($\Psi$, $\Delta$) pair given by:

$$\frac{r_p}{r_s} = \tan\Psi(e^{j\Delta})$$

where $r_p$ and $r_s$ are the complex Fresnel reflection coefficients for the transverse magnetic and transverse electrical waves of the polarized light, respectively. Form the ellipsometry pair ($\Psi$, $\Delta$), the film thickness (t) and index of refraction (n) can be determined. It will be recognized that various ways of analyzing the reflected light may be possible. For example, one alternative is to vary the angle of the quarter wave plate and analyzer to collect polarization information.

Advances in microelectronics fabrication are rapidly surpassing current capabilities in metrology. In order to enable future generations of microelectronics, advanced specific metrology capabilities must be developed. Key among these metrology capabilities is the ability to measure the properties of complex layers of extremely thin films over sub-micron lateral dimensions.

Currently available ellipsometric techniques that measure material properties generally measure them over a large area. In other words, polarization measurements have been traditionally used to determine the thickness and refractive index of homogeneous films over a relatively large area. However, generally, determining the thickness and refractive index of homogeneous films over a relatively large area is inadequate for exceedingly small featured structures. For example, since the polarization state is effected significantly by diffraction from sub-micron features, the shape of such sub-micron features, e.g., critical dimensions of lateral or traverse structures such as gate dielectrics for transistor structures, is difficult to measure using current ellipsometric techniques that determine thickness and refractive index over relatively large areas. For example, the smallest spot that a conventional ellipsometer can measure is generally determined by the beam size, usually on the order of hundreds of microns. This essentially limits the application of conventional ellipsometers to samples with large and uniform interface characteristics.

SUMMARY OF THE INVENTION

The present invention exploits the polarization properties of high numerical aperture lenses to provide a novel ellipsometer, e.g., a micro-ellipsometer or spot ellipsometer. Unlike currently available techniques that measure material properties over a large area, the proposed ellipsometric method and apparatus can produce an ultra-high resolution image of material parameters by scanning a relatively small spot, e.g., sub-micron spot such as a spot smaller than 1 $\mu$m. The proposed technique and apparatus results in accurate polarization measurements of exceedingly small features, providing new measurement capabilities.

Generally, an ellipsometer apparatus according to the present invention is a spot ellipsometer apparatus that uses radial symmetry to attain advantages over conventional techniques. For example, circularly polarized light may be focused to a spot on a sample using an objective lens and reflected therefrom. A radially symmetric ellipsometric signal representative of reflected light may be attained using a radially symmetric analyzer apparatus, e.g., two half-wave plates to produce a pure polarization rotation and a birefringent lens as a radially symmetric analyzer.

An ellipsometry method according to the present invention includes providing radially symmetric polarized light, e.g., radially polarized light or circularly polarized light, incident normal to a sample plane of a sample material. The radially symmetric polarized light is focused to a spot. The sample material reflects at least a portion of the focused radially symmetric polarized light as radially symmetric elliptically polarized light. The radially symmetric elliptically polarized light is operated upon to generate a radially symmetric ellipsometric signal representative of at least one characteristic of the sample material. The radially symmetric ellipsometric signal is detected for use in determining the at least one characteristic of the sample material.

In one embodiment of the method, the method includes operating on the radially symmetric elliptically polarized light to generate a radially symmetric ellipsometric signal using a radially symmetric analyzer. For example, the radially symmetric analyzer may be a birefringent lens, a Brewster angle reflector, or a circular metallic grating.

In another embodiment of the method, a pure polarization rotator may be used in the generation of the radially symmetric ellipsometric signal. For example, the pure polarization rotator may be two-half wave plates, a Faraday rotator, or a rotator including a first quarter wave plate, a variable retarder, and a second quarter wave plate.

In another embodiment of the method, the radially symmetric polarized light is focused to a spot on the sample material using an objective lens. The sample material reflects at least a portion of the focused radially symmetric polarized light as radially symmetric elliptically polarized light. In an alternate embodiment, a solid immersion lens having a lower surface is provided adjacent the sample material. The radially symmetric polarized light is focused to a spot on the lower surface of the solid immersion lens using an objective lens. The sample material reflects at least a portion of the focused radially symmetric polarized light as radially symmetric elliptically polarized light.

An ellipsometer apparatus according to the present invention includes an illumination source operable to provide radially symmetric polarized light, e.g., circularly polarized light or radially polarized light, incident normal to a sample plane of a sample material. An objective lens focuses the radially symmetric polarized light to a spot and collects reflected light from the sample material illuminated using the spot. A radially symmetric analyzer apparatus is adapted to receive the reflected light from the objective lens and provide a focused radially symmetric ellipsometric signal based on the reflected light representative of a characteristic of the sample material. A detector is operable to detect the focused radially symmetric ellipsometric signal for use in determining the at least one characteristic of the sample material.

In various embodiments of the apparatus, the radially symmetric analyzer apparatus may include a pure polarization rotator adapted to receive the reflected light and provide rotated reflected light. Further, the analyzer may include a birefringent lens adapted to focus the rotated reflected light onto the detector, a Brewster angle reflector, or a circular metallic grating.

In another embodiment of the apparatus, the radially symmetric analyzer apparatus includes two half wave plates adapted to receive the reflected light and provide rotated reflected light, a Faraday rotator comprising a Faraday effect material responsive to an applied current adapted to receive the reflected light and provide a rotated reflected light, or pure polarization rotator including a first quarter wave plate, a variable retarder responsive to an applied voltage, and a second quarter wave plate adapted to receive the reflected light and to provide rotated reflected light. Further, the analyzer apparatus may include a radially symmetric analyzer.

In another embodiment, the objective lens is adapted to focus the radially symmetric polarized light to a spot on the sample material. In an alternate embodiment, the apparatus further includes a solid immersion lens having a lower surface positioned adjacent the sample material. The objective lens focuses the radially symmetric polarized light to a spot on the lower surface of the solid immersion lens, e.g., a semi-spherical solid immersion lens.

In another embodiment of the apparatus, the apparatus further includes a first beam splitter for passing the radially symmetric polarized light incident normal to the sample plane and incident on the objective lens. Further, the beam splitter diverts the reflected light collected by the objective lens. A second beam splitter is optically coupled to the first beam splitter to pass the diverted reflected light to the radially symmetric analyzer apparatus. The second beam splitter is adapted to compensate for polarization distortion of the incident radially symmetric polarized light passed by the first beam splitter.

In yet another ellipsometer apparatus according to the present invention, a nulling ellipsometer using radial symmetry is described. In one embodiment of the nulling ellipsometer, the analyzer apparatus of the ellipsometer includes a fixed quarter wave plate, a rotating analyzer, a lens, and a detector, e.g., a charge coupled device camera.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

Radially symmetric ellipsometer apparatus and methods shall be described herein with reference.to FIGS. 2–14, e.g., spot ellipsometer apparatus. In the following detailed description of the embodiments, reference is made to the drawings which form a part thereof, and in which are shown by way of illustration specific embodiments in which the invention may be practiced. It is to be understood that other embodiments may be utilized, as structural or process changes may be made without departing from the scope of the present invention.

Figure 1:
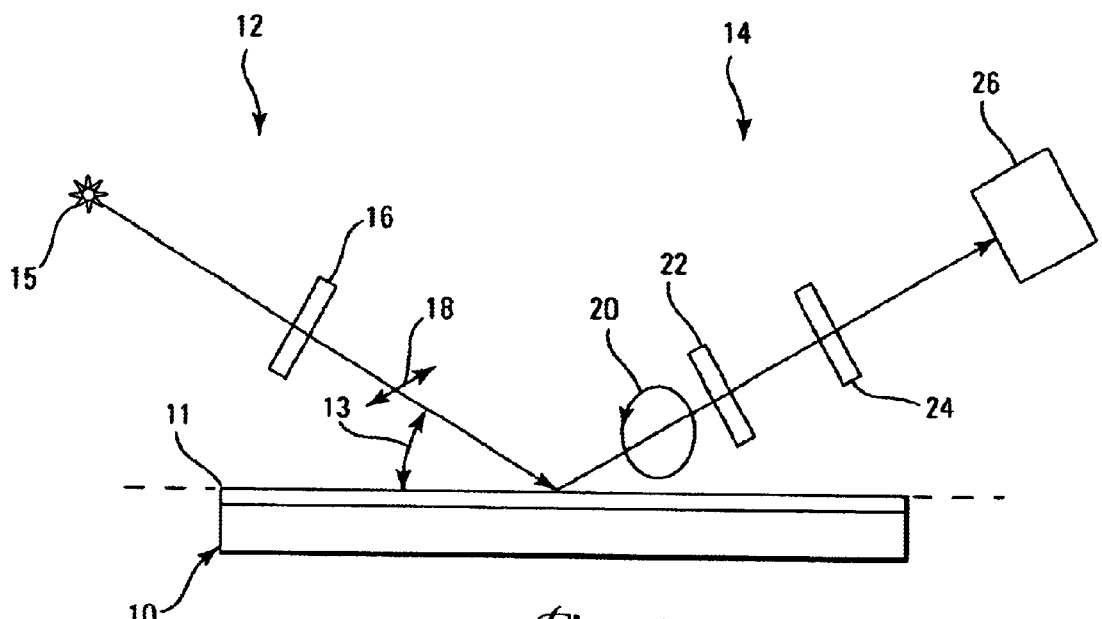
FIG. 1 is a diagram of a conventional ellipsometer.
Figure 2:
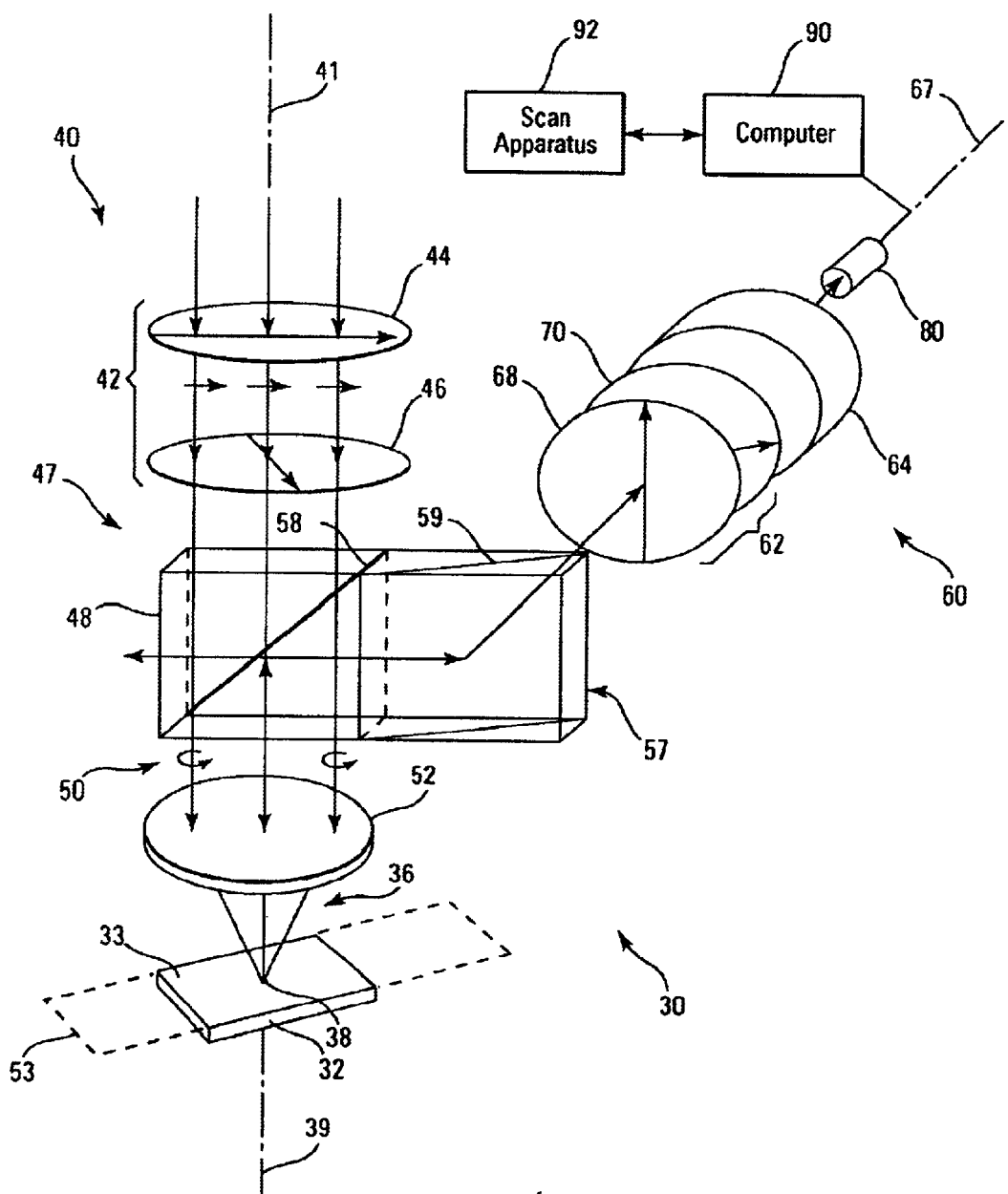
FIG. 2 is one illustrative diagram of an exemplary embodiment of a radially symmetric ellipsometer apparatus according to the present invention.

FIG. 2 shows a radially symmetric ellipsometer apparatus 30 operable for carrying out one or more ellipsometry methods according to the present invention. The ellipsometer apparatus 30 is able to provide or measure an ellipsometric pair ($\psi,\Delta$) of angles such that one or more characteristics of a sample can be determined therefrom, e.g., refractive index (n) and thickness (t). The radially symmetric ellipsometer apparatus 30 according to the present invention is capable of measuring characteristics with respect to very small spots (e.g., submicron spots such as spots smaller than 1 $\mu$m), and therefore, may be referred to as a spot ellipsometer apparatus. For example, characteristics may be determined for submicron features, e.g., critical dimensions of lateral or traverse structures of a sample less than a micron.

With the advent of submicron semiconductor fabrication techniques, characteristics with regard to such submicron features are generally very important. For example, measurement of features such as gate dielectrics for transistor structures in such semiconductor fabrication processes are necessary to produce product.

Under control of computer apparatus 90 and scanning apparatus 92, a small spot may be scanned using any known scanning technique to develop an image from information obtained for a plurality of spots. As scanning of spots is known by those skilled in the art, the present description will not provide any detail description of such a scanning technique as any known scanning equipment and method may be used to provide an image representative of multiple scanned spots. Rather, the following description will provide the basis for providing high resolution information with respect to a small spot of a sample.

Generally, the radially symmetric ellipsometer apparatus 30 uses radial symmetry to provide very high resolution in the measuring of a very small spot 38, preferably, a spot having a diameter less than 1 micron, of a sample 32. An illumination apparatus 40 provides radially symmetric polarized light incident normal to sample plane 33 of a sample 32. The radially symmetric polarized light is focused to spot 38 on the sample plane 33 which is located at the focal plane 53 of the objective lens 52. In other words, the sample plane 33 and the focal plane coincide. The sample plane 33 refers to a surface of the sample 36 to be analyzed. The incident light is normal to the sample plane 33, i.e., the incident plane of the light is normal to the sample plane 33. The sample material 32 reflects at least a portion of the focused radially symmetric polarized light as radially symmetric elliptically polarized light. The reflected light is then used to generate a radially symmetric ellipsometer signal detectable for use in determining one or more characteristics of sample material 32.

Radial symmetry as used herein refers to the symmetry inside an annular region of the ellipsometer apparatus 30 about a particular axis thereof. For example, in the provision of light incident on the objective lens 52, the radially symmetric polarized light from illumination apparatus 40 is radially symmetric about optical axis 39. Likewise, reflected light provided to the analyzer apparatus 60 is radially symmetric about optical axis 67. To be radially symmetric, the optical response of every different angular location within the annular region relative to the axis, e.g., axis 39 and axis 67, is identical to the optical responses of the other angular locations except for phase delay.

The radial symmetry according to the present invention may be thought of in terms of a multiple channel apparatus. In other words, multiple channels parallel to the axes, e.g., axis 39 and axis 67, can be envisioned. Every individual channel located at different angular locations inside a common annular region looks identical to all the others except for phase delay.

In the focusing of incident light onto the sample 32 by the objective lens 52, the interference between these channels forms a high numerical aperture cone of light 36 (with the use of the numerical aperture objective lens 52, e.g., a high numerical aperture objective lens) at the sample plane 33. Such radial symmetry and focusing of such radially symmetric light to the sample plane 33 gives rise to the high resolution of the present apparatus 30. Using the reflected light from the sample 32, the ellipsometric pair ($\psi,\Delta$) corresponding to a small spot 38 (where, as known to those skilled in the art, $\tan(\psi)$ is the ratio of magnitudes of the reflection coefficients for the p-wave and s-wave, and $\Delta$ is the phase difference between the reflection coefficients of the p-wave and s-wave) can be measured. One or more characteristics of the sample material 32, e.g., thickness or index of refraction, may then be deduced therefrom.

The radially symmetric techniques described herein are illustrated by FIG. 2. However, FIG. 2 is only illustrative of one exemplary embodiment of a radially symmetric ellipsometer apparatus 30 according to the present invention. One will recognize that various components thereof may be modified without changing the radially symmetric nature of the ellipsometer apparatus 30. Many different manners of modifying the apparatus 30 shall be described herein with reference to the figures. However, various other modifications without changing the radially symmetric nature of the ellipsometer apparatus are also contemplated in accordance with the scope of the claims hereof.

As shown in FIG. 2, the radially symmetric ellipsometer apparatus 30 includes the illumination apparatus 40, a beam splitter apparatus 47, an objective lens 52, all aligned along axis 39 for use in focusing radially symmetric polarized light to a spot 38 at the sample plane 33 of sample 32. The light focused down to the small spot 38 is reflected from the sample 32 and back for collection by the objective lens 52. The polarization state of the incident light on sample 32 is modified by Fresnel reflection to provide reflected radially symmetric elliptically polarized light that is provided via the beam splitter apparatus 47 to an analyzer apparatus 60 of the radially symmetric ellipsometer apparatus 30.

The analyzer apparatus 60 includes a pure polarization rotator 62, a radial analyzer 64, and a detector 80 aligned along optical axis 67 of the analyzer apparatus 60. The pure polarization rotator 62 maintains the radially symmetric nature of the reflected light representative of the spot 38 on sample 32 which is thereafter focused to the detector 80 by the radial analyzer 64. Through operation upon the reflected radially symmetric elliptically polarized light, e.g., rotation of a component of the pure polarization rotator 62, a radially symmetric ellipsometric signal is detected at the detector 80 from which at least one characteristic of the sample material 32 may be determined. For example, an ellipsometric pair ($\psi,\Delta$) may be derived based on the detected signal at detector 80 using computer apparatus 90 electrically coupled thereto as further described below.

The illumination apparatus 40 may be any illumination device suitable for providing radially symmetric polarized light incident normal to sample plane 33 and thus normal to objective lens 52 which is generally positioned in a parallel manner to sample plane 33. As used herein, radially symmetric polarized light includes, but is clearly not limited to, radially polarized light and circularly polarized light. Any illumination that is radially symmetric in terms of polarization state in the annular region relative to the axis 39 may be suitable for use according to the present invention.

As shown in FIG. 2, the illumination apparatus 40 includes a light source 41 and a circular polarizer apparatus 42. The circular polarizer apparatus 42 includes a polarizer 44 for linearly polarizing light provided by light source 41 and a quarter wave plate 46 for providing suitable polarization to achieve circularly polarized light incident on objective lens 52.

The light source 41 may be any suitable light source at any suitable wavelengths. With use of multiple wavelengths, spectroscopic information may also be obtainable via detection of reflected light and analysis by computer apparatus 90 of the spectrum attained for the multiple wavelengths. Preferably, the light source 41 provides collimated light incident on polarizer 44 of circular polarizer apparatus 42. More preferably, the light source 41 is a laser beam providing precise collimated light. For example, a collimated He—Ne laser may be used to provide the collimated light.

The linear polarizer 44 and quarter wave plate 46 provide circularly polarized light 50. The circularly polarized light 50 passes through a first beam splitter 48 of beam splitter apparatus 47 and is incident on objective lens 52. The beam splitter 48 may introduce some polarization modification to the circularly polarized light provided by quarter wave plate 46. The linear polarizer 44 and quarter wave plate 46 are adjusted to pre-compensate for any such polarization modification introduced by the beam splitter 48. Therefore, the light 50 illuminating the objective lens 52 is circularly polarized such that radial symmetry is achieved in the illumination of sample material 32.

Figure 10:
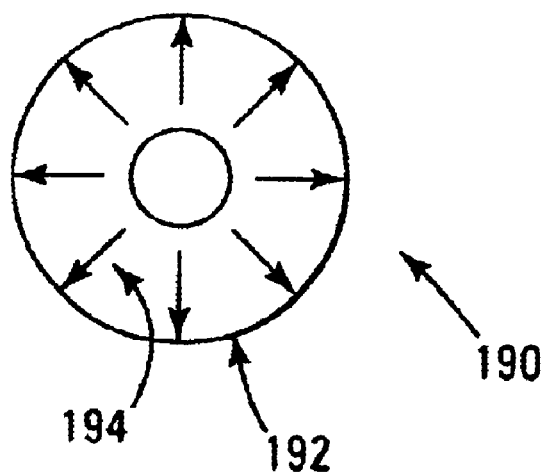
FIG. 10 is a diagram illustrating an alternate illumination source that may be used in the radially symmetric ellipsometer apparatus of FIG. 2.

An alternate embodiment of providing radially symmetric light incident on objective lens 52 is shown in FIG. 10. As shown therein, instead of circularly polarized light, a laser 192, e.g., a HeNe gas laser, providing light with radial polarization is used as the illumination apparatus 40. For example, a laser mode with radial polarization can be generated from a laser directly and used as the illumination source 40 for the radially symmetric ellipsometer apparatus 30. This laser mode with radial polarization 194 is illustrated in FIG. 10.

Although radially polarized light may be used according to the present invention, preferably, the light incident on objective lens 52 is circularly polarized light. Therefore, with respect to the remainder of the description herein the present invention shall be described with respect to circularly polarized light.

With the circularly polarized light 50 incident on objective lens 52, the circularly polarized light forms an aperture cone of light 36 focused at sample plane 33 of sample material 32. Generally, the objective lens 52 is orthogonal to axis 39, as is sample plane 33. The circularly polarized light focused down to a small spot 38 on the sample material 32 is then reflected therefrom, at least in part, as radially symmetric elliptically polarized light. The reflected radially symmetric elliptically polarized light is collected by the objective lens 52 and provided to beam splitter apparatus 47 for diversion to the analyzer apparatus 60 of radially symmetric ellipsometer apparatus 30.

The objective lens 52 is preferably a high numerical aperture objective lens. Preferably, the objective lens 52 has a numerical aperture in the range of 0.5 to less than 1.0. More preferably, the objective-lens 52 has a numerical aperture in the range of 0.8 to less than 1.0. Preferably, for example, the spot 38 is generally of a size falling in the range of 0.25 to 0.5 microns. The size depending, at least in part, on the wavelength of the illumination source.

The reflected light collected by the objective lens 52 is provided to the analyzer apparatus 60 of the ellipsometer apparatus 30 by reflection in beam splitter apparatus 47. Beam splitter apparatus 47 comprises the first beam splitter 48 which passes the circularly polarized light from quarter wave plate 46 to the objective lens 52 for focusing upon the sample material 32, and which provides for reflection and diversion of the reflected elliptically polarized light to analyzer apparatus 60. However, typically, the amplitude reflectivities of the two polarization states, $r_p$ and $r_s$, from a beam splitter such as first beam splitter 48, are different in amplitude and phase. As such, the reflected light will generally pick up some additional ellipticity from the reflection on the beam splitter interface 58 when diverted to analyzer apparatus 60. The amount of this additional ellipticity varies for different incident polarizations. To compensate for such added ellipticity, an identical additional beam splitter 57 is used, as shown in FIG. 2. The additional beam splitter 57 is identical to the beam splitter 48 but rotated in position to provide for such compensation.

Therefore, beam splitter apparatus 47 includes both first beam splitter 48 and second beam splitter 57. First beam splitter 48 includes an interface 58 for reflection of light collected by objective lens 52 normal to the plane of incident light from illumination apparatus 40, i.e., normal to the optical axis 39. The second beam splitter 57 includes an interface 59 for reflection of the diverted light from interface 58 of first beam splitter 48. The reflected light is diverted by the second beam splitter 57 such that the reflected light's direction is orthogonal to the light diverted from interface 58 and also orthogonal to the direction of light from illumination apparatus 40 which is incident on objective lens 52. As such, the s-component for the first beam splitter 48 becomes the p-component for the second beam splitter 57.

Similarly, the p-component for the first beam splitter 48 changes into the s-component for the second beam splitter 57. As a result, the combination of these two beam splitters 48, 57 has the same response to s- and p-components as the reflected light collected at the objective lens 52. As such, the polarization of the incident beam is maintained in the reflected light diverted to the analyzer apparatus 60.

The reflected radially symmetric elliptically polarized light provided to the analyzer apparatus 60 is operated upon by the pure polarization rotator 62 and the radial analyzer 64 such that a radially symmetric ellipsometric signal is provided for detection by detector 80 for use in determining a characteristic of sample material 32. The pure polarization rotator 62 is an angularly independent polarization rotator. In one illustrative embodiment, as shown in FIG. 2, the pure polarization rotator 62 includes two half wave plates 68 and 70.

A half wave plate can be used to rotate the polarization of specific linearly polarized light. However, the amount of rotation depends on the incident polarization. If the incident polarization has an angle ($\theta$) versus the optical axis of the half wave plate, the amount of polarization rotation will be $2\theta$. If the incident polarization has spatial variation, a single half wave plate gives different amounts of rotation for different portions of the light. If two half wave plates, 68 and 70, are combined together, a pure polarization rotation results that is independent of the initial angle. As such, the amount of rotation depends solely on the angle between the optical axis of the two wave plates. This principle is schematically shown in FIG. 3.

Figure 3:
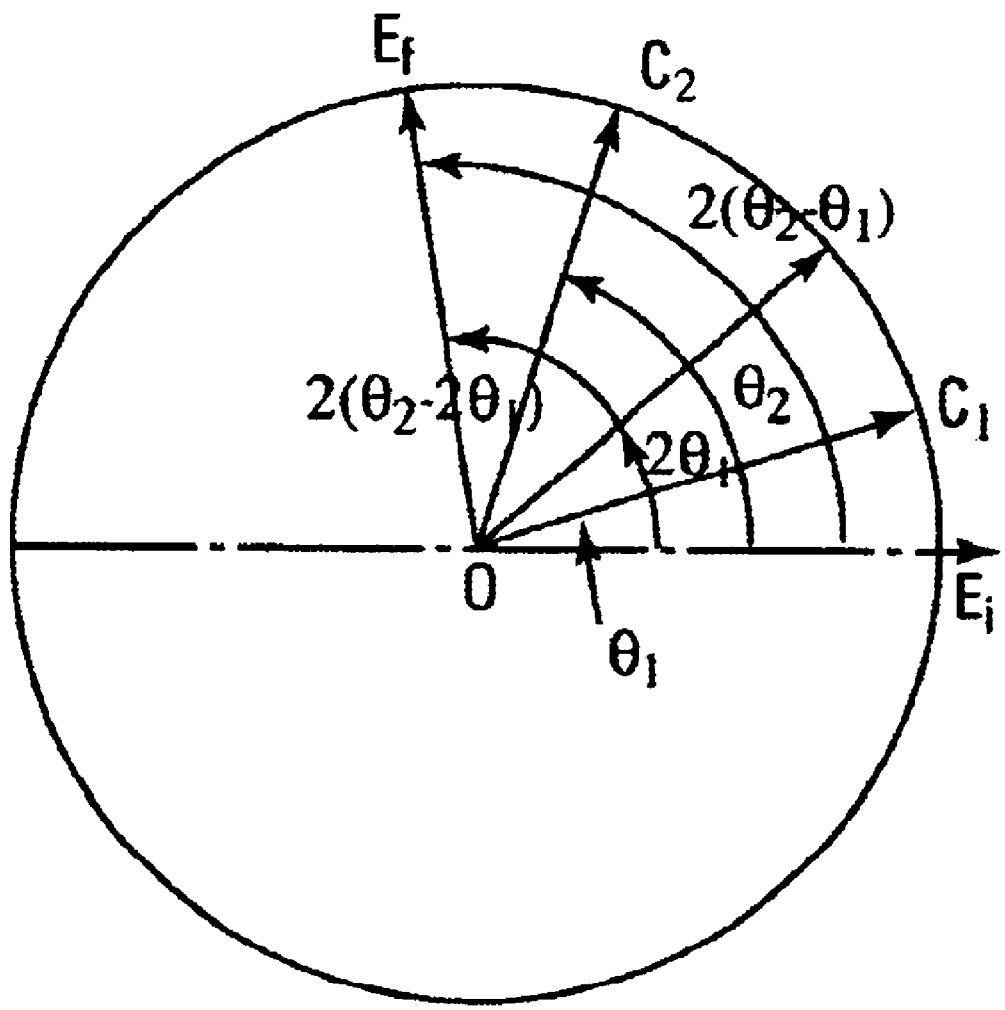
FIG. 3 is an illustrative diagram for use in illustrating a pure polarization rotator used in the radially symmetric ellipsometer apparatus of FIG. 2.

In FIG. 3, $E_i$ and $E_f$ are the initial and final polarization. $C_1$ and $C_2$ are the optical axes for the first and second half wave plates. The amount of rotation from initial to final polarization is $2(\theta_2-\theta_1)$. The principle can be proved mathematically with the Jones calculus.

Denoting a coordinate rotation by $R(\theta_i)$, where, $\theta_i$ is the rotation angle of the $i^{th}$ wave plate, the total effect of the two wave plates T is given by $$T = R(-\theta_2)\begin{pmatrix} 1 & 0 \\ 0 & -1 \end{pmatrix}R(\theta_2)R(-\theta_1)\begin{pmatrix} 1 & 0 \\ 0 & -1 \end{pmatrix}R(\theta_1)$$

$$= \begin{pmatrix} \cos2\theta_2 & \sin2\theta_2 \\ \sin2\theta_2 & -\cos2\theta_2 \end{pmatrix}\begin{pmatrix} \cos2\theta_1 & \sin2\theta_1 \\ \sin2\theta_1 & -\cos2\theta_1 \end{pmatrix}$$

$$= \begin{pmatrix} \cos2(\theta_2-\theta_1) & -\sin2(\theta_2-\theta_1) \\ \sin2(\theta_2-\theta_1) & \cos2(\theta_2-\theta_1) \end{pmatrix} = R(-2(\theta_2-\theta_1))$$

This corresponds to a counterclockwise rotation operation with rotation angle $2(\theta_2-\theta_1)$. The amount of rotation is independent of the incident polarization.

With rotation of at least one of the half wave plates 68, 70 and with use of the radially symmetric analyzer 64 as described below, the radially symmetric ellipsometric signal is provided for detection by detector 80. The reflected intermediate elliptically polarized light provided from the pure polarization rotator 62 to the radial symmetric analyzer 64 is still radially symmetric and must be maintained in such a fashion by radially symmetric analyzer 64, as further described below.

Figure 6:
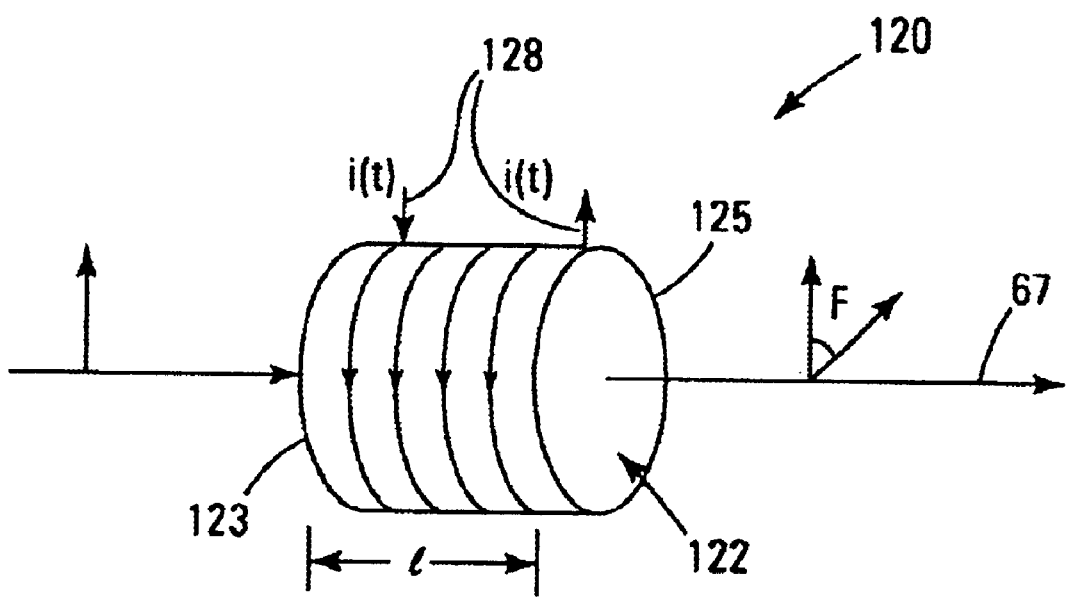
FIG. 6 is a diagram illustrating an alternate pure polarization rotator that may be used in the radially symmetric ellipsometer apparatus of FIG. 2.
Figure 7:
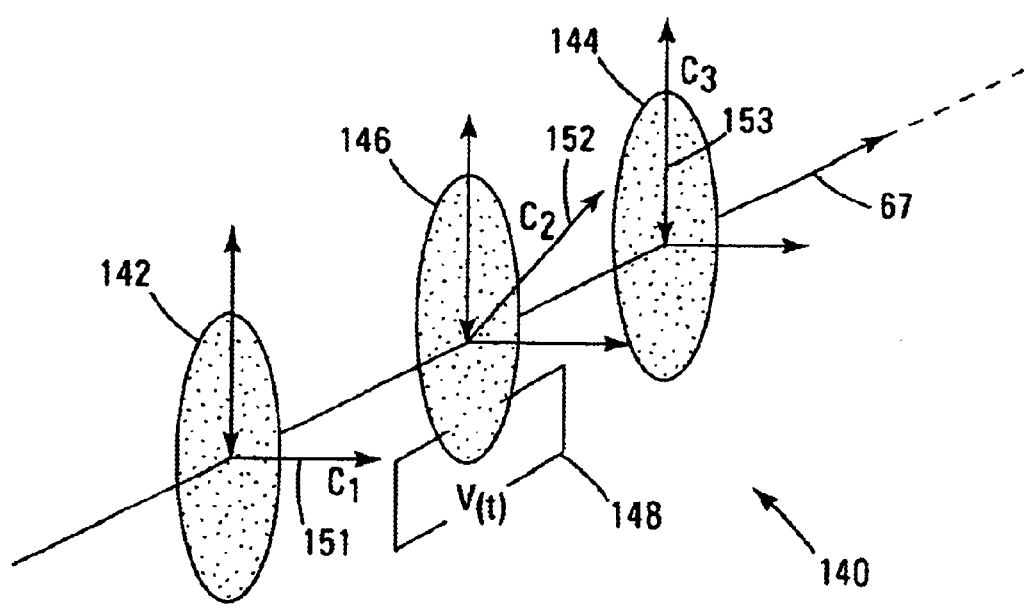
FIG. 7 is an illustrative diagram of another alternate pure polarization rotator which may be used in the radially symmetric ellipsometer apparatus of FIG. 2.

Other alternate illustrative embodiments of pure polarization rotators are shown in FIG. 6 and FIG. 7. For example, the pure polarization rotator 62 may be a Faraday rotator 120 as shown in FIG. 6. The Faraday rotator 120 includes a Faraday effect material 122 responsive to an applied current 128 configured in a generally cylindrical shape along axis 67 extending from a first end 123 to a second end 125. An alternating current (AC) I(t) generates a magnetic field B(t) inside the Faraday effect material 122. When a linearly polarized beam passes through the Faraday rotator 120, its polarization experiences a rotation F(t), where F(t) is proportional to the length (l), i.e., from first end 123 to second end 125, of the Faraday effect material 122 and the magnetic field B(t). Such rotation is also independent of the initial polarization. As such, the Faraday rotator 120 can be used as a pure polarization rotator in the radially symmetric ellipsometer apparatus 30.

Further, as shown in FIG. 7, another alternate pure polarization rotator 140 can be used in the ellipsometer apparatus 30. This pure polarization rotator 140 uses a variable retarder 146 positioned between two quarter wave plates 142 and 144 aligned along the optical axis 67. $C_1$, $C_2$, and $C_3$ (151–153) are the fast axes of the first quarter wave plate 142, the variable retarder 146, and the second quarter wave plate 144, respectively. $C_1$ is perpendicular to $C_3$. The angle between $C_1$ and $C_2$ is 45°. As the rotation applied to the incident light is independent of the incident polarization, the rotator 140 can be used as a pure polarization rotator. The amount of rotation is controlled by the voltage 148 applied to the variable retarder 146.

The variable retarder 146 may be either a liquid crystal variable retarder or an electro-optic crystal variable retarder. The orientation of the fast axes is the same utilizing either type of variable retarder. Further, the voltage 148 applied to an electro-optic crystal variable retarder, like a liquid crystal variable retarder, can be used to control the amount of rotation.

As described above, the radial analyzer 64 of the radially symmetric ellipsometer apparatus 30 must maintain the radial symmetry of the reflected radially symmetric elliptically polarized light. In other words, if one looks at this ellipsometer apparatus 30 as a multiple channel ellipsometer, every channel located at different angular locations inside a common annular region of the radial analyzer must look identical to the others except for phase delay.

Figure 4A:
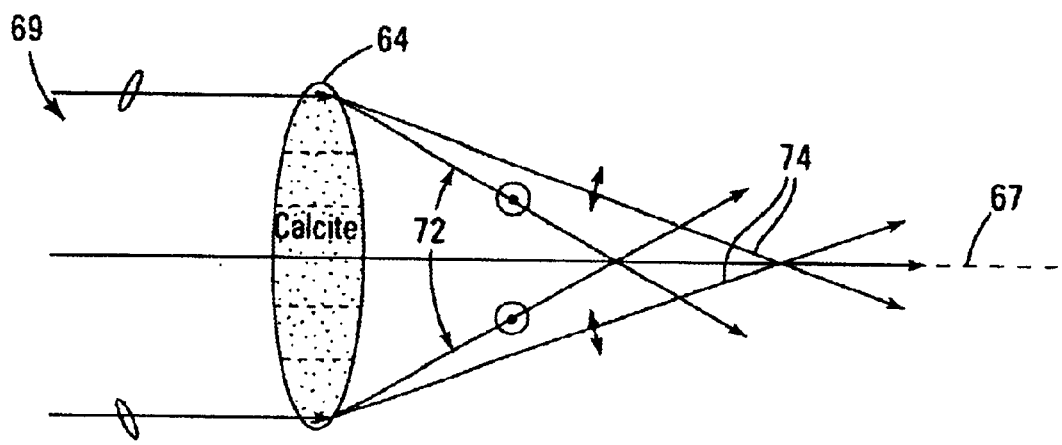
FIG. 4A and FIG. 4B show one illustrative embodiment of a radial analyzer and the function thereof used in the radially symmetric ellipsometer apparatus of FIG. 2.
Figure 4B:
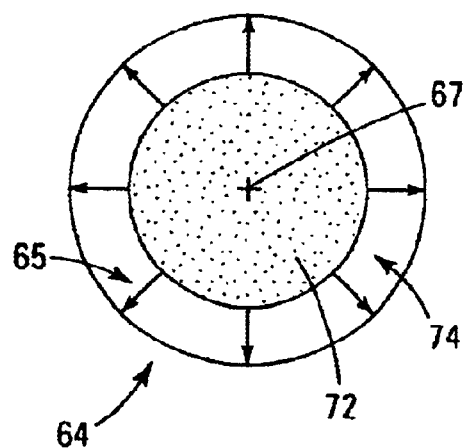

One illustrative embodiment of a radially symmetric analyzer 64 is a birefringent lens as shown in FIG. 2. Such a birefringent lens 64 is shown in further detail in FIG. 4A. When the focus is selected for the extraordinary component 74 of light and blocked for the ordinary component 72 of the light, the birefringent lens 64 acts as a radial analyzer as shown in FIG. 4B. As shown therein, the ordinary component 72 of the light is blocked and the extraordinary component 74 is provided in annular region 65 with radial symmetry about axis 67. The birefringent lens 64, acting as the radial analyzer, focuses the radially symmetric ellipsometric signal on detector 80 positioned at a focal plane thereof for detection.

Figure 8:
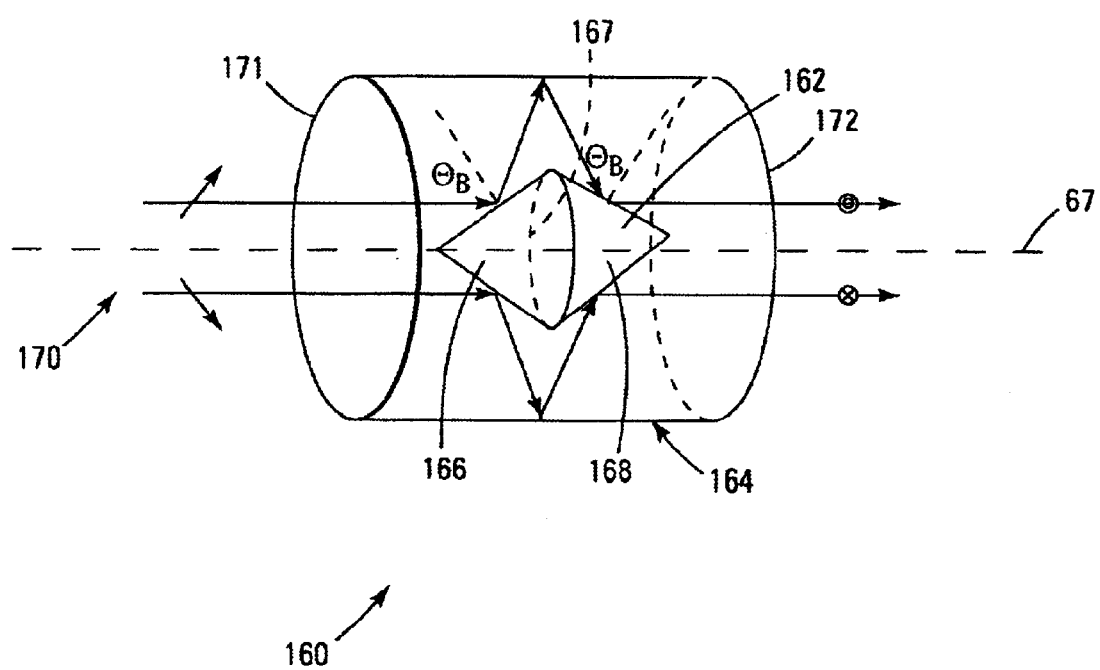
FIG. 8 is an illustrative diagram of an alternate radially symmetric analyzer that may be used in the radially symmetric ellipsometer apparatus of FIG. 2.
Figure 9:
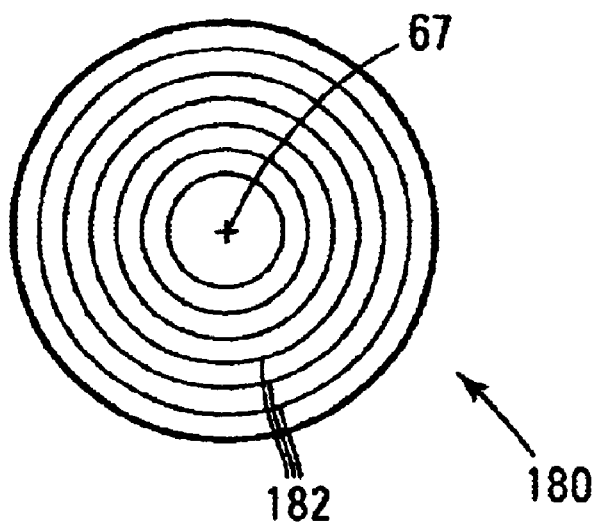
FIG. 9 is yet another illustrative diagram showing an alternate embodiment of a radially symmetric analyzer that may be used in the radially symmetric ellipsometer apparatus of FIG. 2.

FIGS. 8 and 9 provide alternate radially symmetric analyzers for use in ellipsometer apparatus 30. As shown in FIG. 8, an alternate radial analyzer 160 includes a Brewster angle reflector. The alternate radial analyzer 160 comprises a metal tube reflector 164 extending along axis 67 from a first end 171 to a second end 172. A cone reflector 162 is positioned within the metal tube reflector 164 along axis 67. The cone reflector 162 is made of a dielectric material suitable for absorbing light. The cone reflector 162 comprises a first cone 166 and a second cone 168 in opposing relationship along axis 67. The two cones 166 and 168 interface at plane 167 orthogonal to the axis 67.

When the incident angle of light 170 is equal to the Brewster angle ($\Theta_B$), the reflected light will be polarized perpendicular to the incident plane. Light transmitted into the cone reflector 162 is absorbed while the remaining light passes therethrough with the maintenance of radial symmetry. With use of this alternate radial analyzer 160, a lens aligned along the axis 67 may be used to focus the light provided thereby to the detector 80 or a large area detector may be used to receive the light and provide suitable signals to computer apparatus 90.

Another alternate radial analyzer is shown in FIG. 9. This metallic grating radial analyzer 180 includes a plurality of circular gratings 182 with subwavelength periods about axis 67. Such a circular metallic grating with subwavelength periods can be also be used as the radial analyzer of the ellipsometer apparatus 30. With use of this alternate radial analyzer 180, a lens aligned along the axis 67 may be used to focus the light provided thereby to the detector 80 or a large area detector may be used to receive the light and provide suitable signals to computer apparatus 90.

Detector 80 of analyzer apparatus 60 is a photodetection device such as one or more photodiodes. Further, the detector 80 may be a charge coupled device detector (CCD). Any suitable detector for detecting the intensity of light and providing a signal representative thereof may be used according to the present invention.

With the radially symmetric ellipsometer apparatus 30 configured as shown in FIG. 2 or configured with one or more modifications as otherwise described herein, a desired signal can be achieved such that the ellipsometric pair ($\psi, \Delta$) can be deduced from the signal impinging on detector 80 and provided to computer apparatus 90. Such functionality can be described in mathematical terms as given below.

Figure 5:
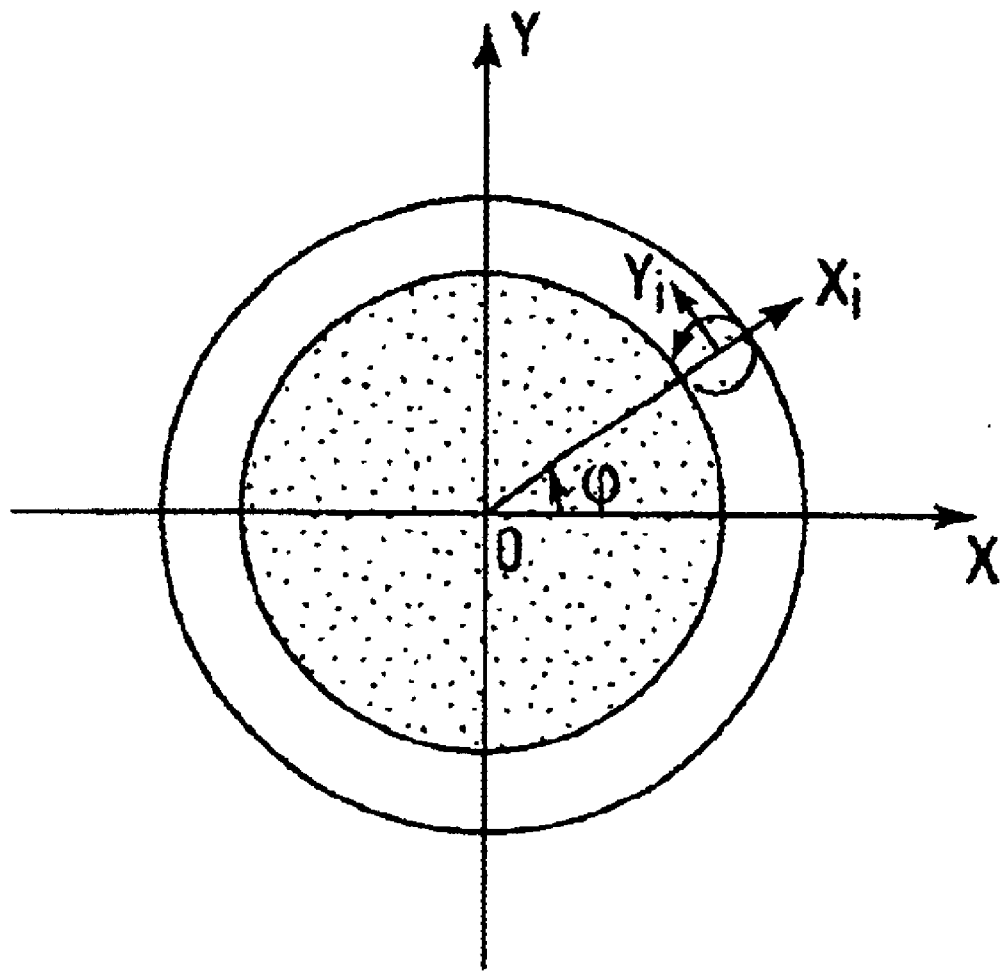
FIG. 5 shows one illustrative diagram for use in describing the functionality in mathematical terms of the radially symmetric ellipsometer apparatus of FIG. 2.

The coordinate system at the pupil plane is shown in FIG. 5. A circularly polarized plane wave is incident on the objective lens in laboratory coordinate frame (xoy). Its Jones vector is $$E_{in} = \begin{pmatrix} 1 \\ j \end{pmatrix}$$

Consider one ray that enters the pupil at azimuth angle $\phi$. This ray can be viewed as an individual channel. The coordinate system of this channel is $x_i o y_i$, as shown in FIG. 5. This coordinate system is chosen such that the two eigen vectors align with the s and p directions when this ray hits the sample. The incident polarization in this local coordinate system is $$E = R(\varphi)E_{in} = \begin{pmatrix} \cos\varphi & \sin\varphi \\ -\sin\varphi & \cos\varphi \end{pmatrix} \begin{pmatrix} 1 \\ j \end{pmatrix} = e^{j\varphi} \begin{pmatrix} 1 \\ j \end{pmatrix}$$

This indicates that each channel sees circularly polarized light with a phase shift. After the reflection from the sample, this circularly polarized light will generally become elliptically polarized, due to the Fresnel reflection at the sample interface. Because of the radial symmetry, each channel will have identical elliptically polarized light, except that each ellipse is rotated by $\phi$ and delayed by $e^{j\Phi}$. In each local coordinate system $x_i o y_i$, the ellipse has ellipticity $\epsilon$ and its semi-longitudinal axis has angle $\theta_0$ with respect to $ox_i$. Thus the polarization for this channel can be written as $$E'(\varphi) = e^{j\varphi} R(-\theta_0) \begin{pmatrix} \cos\varepsilon \\ j\sin\varepsilon \end{pmatrix}$$

This is the Jones vector in the local coordinate system. The Jones vector in laboratory coordinate system is $$E(\varphi) = R(-\varphi)E'(\varphi) = e^{j\varphi} R(-(\theta_0 + \varphi)) \begin{pmatrix} \cos\varepsilon \\ j\sin\varepsilon \end{pmatrix}$$

Then the beam goes through a pure polarization rotator described above. The polarization of each channel is rotated by the same amount F. The polarization for one channel becomes $$E(\varphi) = R(F)e^{j\varphi} R(-(\theta_0 + \varphi)) \begin{pmatrix} \cos\varepsilon \\ j\sin\varepsilon \end{pmatrix} = e^{j\varphi} R(F - (\theta_0 + \varphi)) \begin{pmatrix} \cos\varepsilon \\ j\sin\varepsilon \end{pmatrix}$$

Then this beam passes through the radial polarizer $$E(\varphi) = \begin{pmatrix} 1 & 0 \\ 0 & 0 \end{pmatrix} R(\varphi)e^{j\varphi} R(F - (\theta_0 + \varphi)) \begin{pmatrix} \cos\varepsilon \\ j\sin\varepsilon \end{pmatrix} = e^{j\varphi} \begin{pmatrix} 1 & 0 \\ 0 & 0 \end{pmatrix}$$

$$R(F - \theta_0) \begin{pmatrix} \cos\varepsilon \\ j\sin\varepsilon \end{pmatrix}$$

$$= e^{j\varphi} \begin{pmatrix} \cos(F - \theta_0)\cos\varepsilon + j\sin(F - \theta_0)\sin\varepsilon \\ 0 \end{pmatrix}$$

With use of a power meter after the radial analyzer to detect the signal, due to the power conservation, the signal will be $$P \propto \int_0^{2\pi} |E(\varphi)|^2 \, d\varphi = \int_0^{2\pi} [\cos^2(F-\theta_0)\cos^2\varepsilon + \sin^2(F-\theta_0)\sin^2\varepsilon] \, d\varphi$$
$$= 2\pi[\cos^2(F-\theta_0)\cos^2\varepsilon + \sin^2(F-\theta_0)\sin^2\varepsilon]$$

It can be simplified as $$P = K\{1 + \cos 2\varepsilon \cos[2(\theta_0 - F)]\}$$

where K is a constant that contains effects like detector efficiency, reflection loss from optical components, etc.

From the expression of the signal P, $\varepsilon$ and $\theta_0$ can be obtained by measuring P for several different rotation angles F. If the polarization rotator is rotated at a constant angular speed, the resultant signal is a sinusoidal signal. By measuring the amplitude and phase of this sinusoidal signal, $\varepsilon$ and $\theta_0$ can be calculated. From these two values, the corresponding $(\Psi, \Delta)$ pair of the illuminated micro-spot can be derived.

$$R(-\theta_0)\begin{pmatrix} \cos\varepsilon \\ j\sin\varepsilon \end{pmatrix} = \begin{pmatrix} r_s & 0 \\ 0 & r_p \end{pmatrix}\begin{pmatrix} 1 \\ j \end{pmatrix} = \begin{pmatrix} r_s \\ jr_p \end{pmatrix}$$

$$\frac{r_p}{r_s} = \tan\Psi \cdot e^{j\Delta}$$

From these two equations, the ellipsometric geometries $(\Psi, \Delta)$ can be obtained in terms of $(\varepsilon, \theta_0)$ by:

$$\tan^2\Psi = \frac{\sin^2\theta_0\cos^2\varepsilon + \cos^2\theta_0\sin^2\varepsilon}{\cos^2\theta_0\cos^2\varepsilon + \sin^2\theta_0\sin^2\varepsilon}$$

$$\Delta = \tan^{-1}\left(\frac{\tan\varepsilon}{\tan\theta_0}\right) + \tan^{-1}(\tan\theta_0\tan\varepsilon) - \frac{\pi}{2}$$

With further reference to FIG. 2, the computer apparatus 90 runs software that allows the user to control the spot ellipsometer apparatus 30 by means of a graphical user interface (not shown) and is generally used to control the ellipsometer apparatus 30 and perform digital processing with respect to the signal detected by detector 80. For example, the computer apparatus 90 may be used to control rotation of any of the components described herein (e.g., rotation of a half wave plate in the pure polarization rotator 62), may be used to control application of the voltage to the pure polarization rotator such as described with reference to FIG. 7, may be used to deduce ellipsometric pairs for the signal detected by detector 80 of ellipsometer apparatus 30, or control any other components of the apparatus 30 interfaced to the computer, such as any microcontrollers, scanning apparatus 92, etc. For example, as described above, the spot 38 can be scanned under control of the computer apparatus 90 to produce polarization information with respect to multiple spots. Such multiple spot information may be used by the computer apparatus 90 to generate a mapped image.

Further, computer apparatus 90 includes software for providing data visualization and analysis capabilities via user control. For example, graphical illustrations of the thickness of a thin layer of sample material 32 may be shown graphically after digital processing of any number of spots 38. In addition, spectroscopic information may be available upon use of any number of different wavelengths, as would be known to one skilled in the art. The computer apparatus 90 may be any standard computer apparatus such as a computer apparatus operating Windows or Windows NT.

In one illustrative manner of determining thickness and index of refraction using an ellipsometric pair $(\psi, \Delta)$, computer apparatus 90 includes memory having a look-up table relating the ellipsometric pairs to thickness and index of refraction. For example, a computer program may be used to generate the $\psi$ and $\Delta$ trajectories for various indices and thicknesses. These results are stored in a look-up table in the computer memory of computer apparatus 90. When ellipsometric parameters are measured for a sample material 32, the computer apparatus 90 may search the look-up table and do an interpolation and regression computation to find a corresponding index of refraction (n) and thickness (t). Further, alternatively, multi-variable regression analysis may be used in determining such parameters.

In the system described above, if the annular aperture is narrow enough so that the angle of incidence can be approximated as a single value, the identical look-up table can be used. Otherwise, integration of a signal in a radial direction during simulation or model production would be needed to generate a look up table such that suitable correlation between the ellipsometric pair and characteristics such as thickness and index of refraction can be attained.

The single spot mode can be used to measure the thickness and refractive indices at both sides of an edge of a structure of the sample 32, thus greatly reducing the number of parameters necessary to characterize the edge. For example, to characterize a sharp transition region, many parameters, such as thickness, refraction indices, slope, undercutting, etc. are needed. The structure of the transition region can be determined by performance of model fitting using such parameters. However, with the use of larger numbers of parameters, the larger the solution space for the model fitting and the more difficult the model fitting becomes. After a measurement is performed according to the present invention by applying the spot ellipsometer to measure thicknesses and refraction indices beside the sharp transitions, the number of parameters is greatly reduced. This makes model fitting less complex and more feasible.

Figure 11:
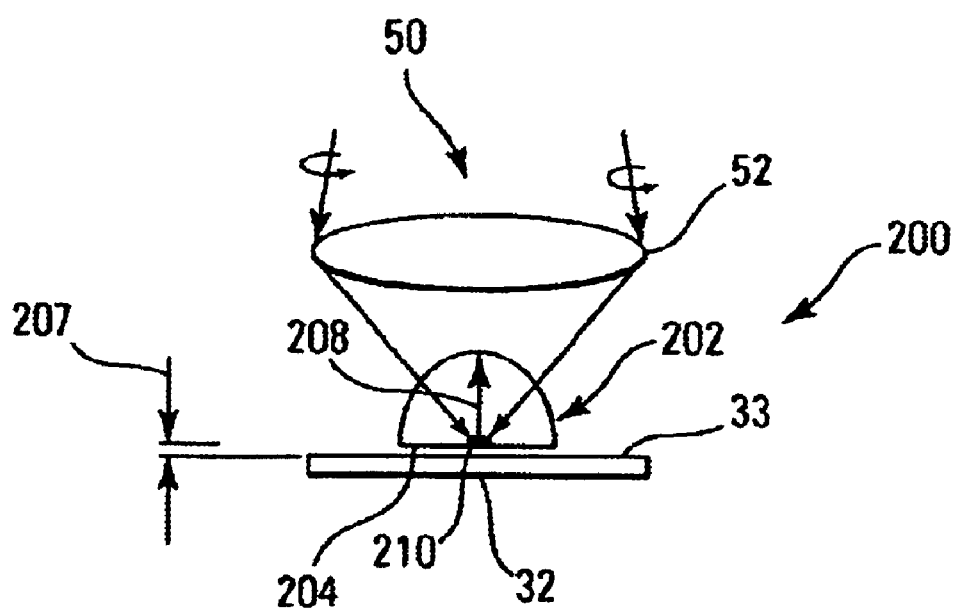
FIG. 11 is an illustrative diagram of near field optics, e.g., a solid immersion lens, that may be used in combination with the radially symmetric ellipsometer apparatus of FIG. 2.

The ellipsometer apparatus 30 provides high resolution, however, to even further increase the resolution, near field optics 200 can be employed in the near field of the sample material 32 to decrease the spot size of the ellipsometer apparatus 30. As shown in FIG. 11, a solid immersion lens (SIL) 202 may be positioned between the objective lens 52 and sample material 32. Generally, the solid immersion lens 202 is a semispherical solid immersion lens, although other solid immersion lens may be feasible with modifications to the apparatus 30. Preferably, the semispherical solid immersion lens 202 includes a lower surface 204 that is generally planer and an opposing surface having a radius (r) 208. Preferably, the radius 208 is in the range of several millimeters.

The lower surface 204 is positioned adjacent the sample plane 33. The lower surface 204 may be positioned directly adjacent and in contact with the sample material 32 at sample plane 33. However, preferably the lower surface 204 is positioned with a space or gap 207 having a height (h) in a range of less than 10 nanometers between the sample plane 33 of the sample 32 and the lower surface 204 of the solid immersion lens 202.

The solid immersion lens 202 is formed of a material having a high index of refraction. Preferably, the refraction index may be in the range of 2 to 4. For example, the solid immersion lens 202 may be formed of GaP which has an index of refraction of about 3.5.

The light illuminating the objective lens 52 is focused onto the bottom or lower surface 204 of the solid immersion lens 202. The light focused down to lower surface 204 forms a tight spot 210 thereon. The optical coupling between the light focused on the lower surface 204 of the solid immersion lens 202 and the sample material 32 produces a reflection captured by objective lens 52. For example, the spot may be about 0.1 microns. The spot size depends, at least in part, on the wavelength used in the apparatus.

Figure 12:
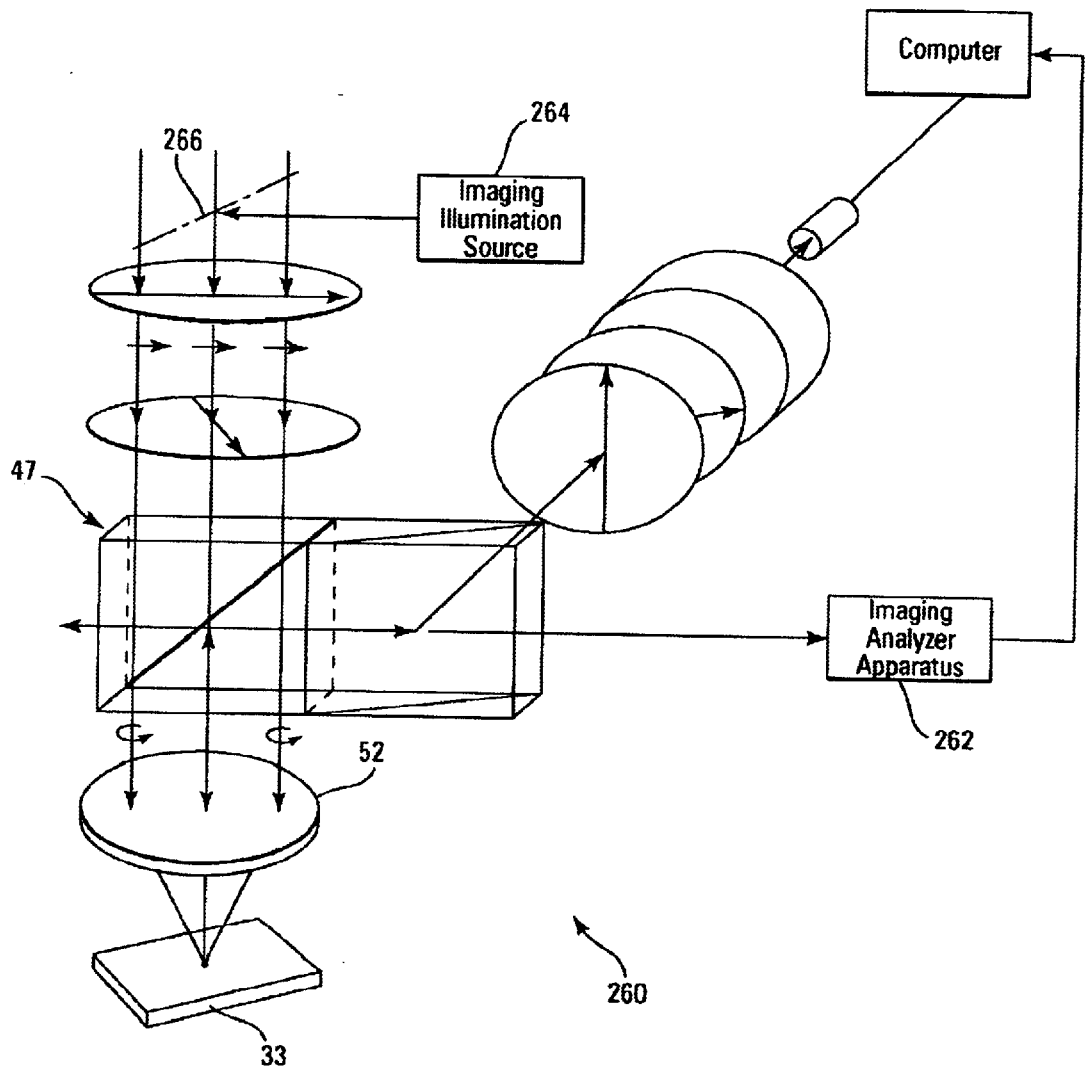
FIG. 12 is an illustrative diagram showing the radially symmetric ellipsometer apparatus of FIG. 2 in combination with an imaging apparatus for use in an imaging mode operable with use of at least the objective lens of the radially symmetric ellipsometer apparatus of FIG. 2.

FIG. 12 shows an ellipsometer apparatus 260 substantially the same as that shown in FIG. 2 with the addition of several block components such that an imaging ellipsometer like that described in copending U.S. patent application Ser. No. 09/691,006, entitled "Imaging Ellipsometry," filed on the same day herewith and incorporated by reference herein in its entirety, can be configured and used in an imaging mode. In the imaging mode, the imaging ellipsometer can use one or more components of the present radially symmetric ellipsometer apparatus. In other words, one or more of the components can be commonly used by both types of ellipsometers.

As shown in FIG. 12, ellipsometer apparatus 260 includes a beam splitter 266 for coupling an illumination source 264 into the apparatus to provide linearly polarized light to beam splitter apparatus 47 for illumination of objective lens 52 and focusing to a sample material 33 in an imaging mode such as described in the above co-pending application. The components providing circularly polarized light 42 would be removed from the optical path during the imaging mode. The reflected light in the imaging mode would be collected by objective lens 52 diverted by beam splitter 47 to an imaging mode analyzer 262. Such an analyzer 262 may be similar to the analyzer described in the above-mentioned copending application.

In this manner, both an imaging mode and a spot mode can be carried out during different time periods using common components such as the objective lens 52. Further, the imaging mode may be used to image a large area such that a spot can be selected for imaging using the spot ellipsometer apparatus according to the present invention as described herein. In other words, the larger area imaging may be used to determine where to focus the spot on sample plane 33 for further and more detailed analysis.

Figures 13, 14:
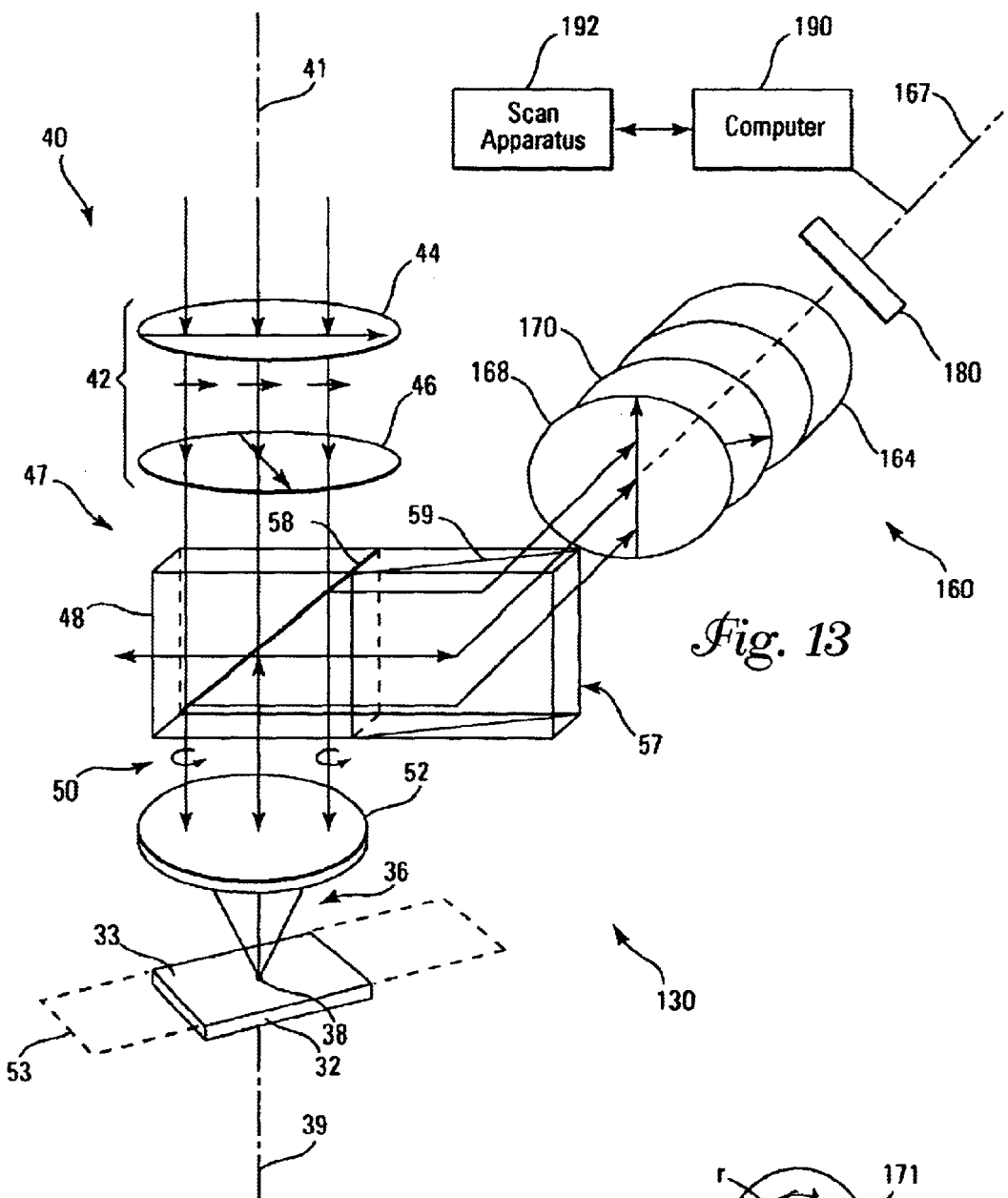
FIG. 13 is an illustrative diagram showing a nulling ellipsometer apparatus using radial symmetry.
FIG. 14 is a diagram for use in describing the nulling ellipsometer apparatus of FIG. 13.

FIG. 13 shows another embodiment of an ellipsometer apparatus 130 that uses radial symmetry according to the present invention to provide one or more characteristics of sample 32. The nulling ellipsometer apparatus 130 is configured in substantially the same manner as the ellipsometer apparatus 30 of FIG. 2, except for the analyzer apparatus 160. Therefore, the same reference numbers are utilized for the similar components in FIG. 13 and no detail with regard to such components shall be provided with reference to FIG. 13. Instead of the pure polarization rotator 62 and birefringent lens 64 shown in the apparatus 30 of FIG. 2, the nulling ellipsometer apparatus 130 shown in FIG. 13 includes an analyzer apparatus 160 which includes a fixed quarter wave plate 168, a rotating analyzer 170, a lens 164, and a CCD camera 180.

Radial symmetry allows the nulling ellipsometer 130 to operate as follows. Due to the use of circularly polarized illumination 50, and the two beam splitter apparatus 47, the reflected light after the beam splitter 57 that is provided to the analyzer apparatus 160 is ellipsometrically radially symmetric just as described with reference to FIG. 2. If a centered annular ring 171 of the light is considered as shown in FIG. 14, the polarization state of each point in the ring is the same, except that the major axis of the ellipse of the polarization state is continuously rotated. Therefore, as the light passes through the fixed quarter wave plate 168, the polarization states of two opposite positions in the ring 171 will become linearly polarized. When the light passes through the rotating analyzer 170, at certain angular positions of the analyzer 170, the orientation of the analyzer 170 is perpendicular to the linear polarization state of the above mentioned two points. Therefore, the light is nulled at these two points.

The light then passes through the lens 164 and is imaged on a CCD camera 180. The corresponding nulled positions form two minimums of the image captured by the camera 180. From the radial positions of the nulling points, the corresponding incident angle on the sample 32, e.g., a thin film, can be found. By rotating the analyzer 170 and recording a sequence of images from the camera 180, the radial position of the nulled points and the corresponding angular position of the analyzer 170 can be obtained. Since the quarter wave plate 168 is fixed, its angular position is known. With the known incident angle, the known angular position of the quarter wave plate 168, and the known angular position of the rotating analyzer 170, the sample, e.g., thin film, characteristics can be calculated using conventional nulling ellipsometry calculation techniques.

There is no need to block the center of the light using the nulling technique. This is unlike the technique described with respect to FIG. 2. In the nulling technique, all the light, e.g., the whole beam, is imaged onto the CCD camera 180. For those annular rings inside the light that have different radii, the nulling points will have different corresponding angular positions of the analyzer 170. Likewise, different radii mean different incident angles on the sample. As such, by recording a complete sequence of images of the light, multi-angle incidence ellipsometry can be performed. Thus, the ellipsometer apparatus 130 can be used as a nulling multi-angle incidence micro-spot ellipsometer.

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. An ellipsometry method comprising:
   providing radially symmetric polarized light incident normal to a sample plane of a sample material;
   focusing the radially symmetric polarized light to a spot, wherein the sample material reflects at least a portion of the focused radially symmetric polarized light as radially symmetric elliptically polarized light;
   operating on the radially symmetric elliptically polarized light to generate a radially symmetric ellipsometric signal, wherein operating on the radially symmetric elliptically polarized light comprises modifying polarization of the radially symmetric elliptically polarized light to generate a radially symmetric ellipsometric signal, wherein such modification maintains radial symmetry of the radially symmetric elliptically polarized light; and
   detecting the radially symmetric ellipsometric signal for use in determining at least one characteristic of the sample material.

2. The method of claim 1, wherein providing radially symmetric polarized light comprises providing circularly polarized light.

3. The method of claim 1, wherein providing radially symmetric polarized light comprises providing radially polarized light.

4. The method of claim 1, wherein operating on the radially symmetric elliptically polarized light to generate a radially symmetric ellipsometric signal comprises using a birefringent lens to generate the radially symmetric ellipsometric signal.

5. The method of claim 1, wherein operating on the radially symmetric elliptically polarized light to generate a radially symmetric ellipsometric signal comprises using a Brewster angle reflector to generate the radially symmetric ellipsometric signal.

6. The method of claim 1, wherein operating on the radially symmetric elliptically polarized light to generate a radially symmetric ellipsometric signal comprises using a circular metallic grating to generate the radially symmetric ellipsometric signal.

7. The method of claim 1, wherein operating on the radially symmetric elliptically polarized light to generate a radially symmetric ellipsometric signal comprises:

passing the reflected radially symmetric elliptically polarized light through two half wave plates to provide an intermediate reflected light incident on a radially symmetric analyzer;

rotating at least one of the half wave plates; and providing the intermediate reflected light using the radially symmetric analyzer as the radially symmetric ellipsometric signal onto a detector.

8. The method of claim 1, wherein operating on the radially symmetric elliptically polarized light to generate a radially symmetric ellipsometric signal comprises:

passing the radially symmetric elliptically polarized light through a Faraday rotator comprising a Faraday effect material to provide an intermediate reflected light incident on a radially symmetric analyzer;

applying a current source to the Faraday effect material; and providing the intermediate reflected light using the radially symmetric analyzer as the radially symmetric ellipsometric signal onto a detector.

9. The method of claim 1, wherein operating on the radially symmetric elliptically polarized light to generate a radially symmetric ellipsometric signal comprises:

passing the radially symmetric elliptically polarized light through a first quarter wave plate, a variable retarder, and a second quarter wave plate to provide an intermediate reflected light incident on a radially symmetric analyzer;

applying a voltage to the variable retarder; and providing the intermediate reflected light using the radially symmetric analyzer as the radially symmetric ellipsometric signal onto a detector.

10. The method of claim 9, wherein the variable retarder comprises a liquid crystal variable retarder.

11. The method of claim 9, wherein the variable retarder comprises an electro-optic crystal variable retarder.

12. The method of claim 1, wherein focusing the radially symmetric polarized light to a spot comprises focusing the radially symmetric polarized light to a spot on the sample material using an objective lens, wherein the sample material reflects at least a portion of the focused radially symmetric polarized light as radially symmetric elliptically polarized light.

13. The method of claim 1, wherein focusing the radially symmetric polarized light to a spot comprises:

providing a solid immersion lens, the solid immersion lens having a lower surface adjacent the sample material; and focusing the radially symmetric polarized light to a spot on the lower surface of the near field lens using an objective lens, wherein the sample material reflects at least a portion of the focused radially symmetric polarized light as radially symmetric elliptically polarized light.

14. The method of claim 1, wherein the method further comprises imaging a portion of the sample material to determine a spot portion of the sample from which at least a portion of the focused radially symmetric polarized light is to be reflected.

15. An ellipsometer apparatus comprising:

an illumination source operable to provide radially symmetric polarized light incident normal to a sample plane of a sample material;

an objective lens to focus the radially symmetric polarized light to a spot and to collect reflected light from the sample material illuminated using the spot;

a radially symmetric analyzer apparatus adapted to receive the reflected light from the objective lens and provide a radially symmetric ellipsometric signal based on the reflected light representative of a characteristic of the sample material, wherein the radially symmetric analyzer apparatus is further adapted to modify polarization of the reflected light while maintaining radial symmetry; and a detector to detect the radially symmetric ellipsometric signal for use in determining at least one characteristic of the sample material.

16. The apparatus of claim 15, wherein the illumination source is operable to provide circularly polarized light.

17. The apparatus of claim 15, wherein the illumination source is operable to provide radially polarized light.

18. The apparatus of claim 15, wherein the radially symmetric analyzer apparatus comprises:

a pure polarization rotator adapted to receive the reflected light and provide rotated reflected light; and a birefringent lens adapted to focus the rotated reflected light onto the detector.

19. The apparatus of claim 15, wherein the radially symmetric analyzer apparatus comprises:

a pure polarization rotator adapted to receive the reflected light and provide rotated reflected light; and a Brewster angle reflector adapted to provide the rotated reflected light to the detector.

20. The apparatus of claim 15, wherein the radially symmetric analyzer apparatus comprises:

a pure polarization rotator adapted to receive the reflected light and provide rotated reflected light; and a circular metallic grating adapted to provide the rotated reflected light to the detector.

21. The apparatus of claim 15, wherein the radially symmetric analyzer apparatus comprises:

two half wave plates adapted to receive the reflected light and provide rotated reflected light; and a radially symmetric analyzer to provide the rotated reflected light onto the detector.

22. The apparatus of claim 15, wherein the radially symmetric analyzer apparatus comprises:

a Faraday rotator comprising a Faraday effect material responsive to an applied current adapted to receive the reflected light and provide a rotated reflected light; and a radially symmetric analyzer to provide the rotated reflected light onto the detector.

23. The apparatus of claim 15, wherein the radially symmetric analyzer apparatus comprises:

a first quarter wave plate, a variable retarder responsive to an applied voltage; and a second quarter wave plate adapted to receive the reflected light and to provide rotated reflected light; and a radially symmetric analyzer to provide the rotated reflected light onto the detector.

24. The apparatus of claim 23, wherein the variable retarder comprises a liquid crystal variable retarder responsive to an applied voltage.

25. The apparatus of claim 23, wherein the variable retarder comprises an electro-optic crystal variable retarder responsive to an applied voltage.

26. The apparatus of claim 15, wherein the objective lens is adapted to focus the radially symmetric polarized light to a spot on the sample material, wherein the sample material reflects at least a portion of the focused radially symmetric polarized light as radially symmetric elliptically polarized light.

27. The apparatus of claim 15, wherein the apparatus further comprises a solid immersion lens positioned adjacent the sample material, the solid immersion lens having a lower surface, wherein the objective lens focuses the radially symmetric polarized light to a spot on the lower surface of the solid immersion lens, wherein the sample material reflects at least a portion of the focused radially symmetric polarized light as the reflected light.

28. The apparatus of claim 27, wherein the solid immersion lens is a semi-spherical solid immersion lens.

29. The apparatus of claim 15, wherein the illumination source comprises a circular polarization apparatus to provide circularly polarized light incident normal to the sample plane.

30. The apparatus of claim 29, wherein the circular polarizer apparatus comprises:

a polarizer positioned to receive light from a light source and to linearly polarize the light; and a quarter wave plate to circularly polarize the linearly polarized light.

31. The apparatus of claim 15, wherein the illumination source comprises a laser beam apparatus operable to provide radially polarized light.

32. The apparatus of claim 15, wherein the apparatus further comprises:

a first beam splitter for passing the radially symmetric polarized light incident normal to the sample plane and incident on the objective lens, and further wherein the beam splitter diverts the reflected light collected by the objective lens; and a second beam splitter optically coupled to first beam splitter to pass the diverted reflected light to the radially symmetric analyzer apparatus, wherein the second beam splitter is adapted to compensate for polarization distortion of the incident radially symmetric polarized light passed by the first beam splitter.

33. The apparatus of claim 15, wherein an imaging ellipsometer apparatus is operable to image a portion of the sample material using at least the objective lens of the apparatus when not being used to focus the radially symmetric polarized light to a spot.

34. The method of claim 1, wherein operating on the radially symmetric elliptically polarized light comprises operating on the radially symmetric elliptically polarized light over a period of time while maintaining radial symmetry to generate a radially symmetric signal.

* * * * *

UNITED STATES PATENT AND TRADEMARK OFFICE
CERTIFICATE OF CORRECTION

PATENT NO. : 6,693,711 B1
DATED : February 17, 2004
INVENTOR(S) : Leger et al.

It is certified that error appears in the above-identified patent and that said Letters Patent is hereby corrected as shown below:

<u>Title page,</u>
Item [12], delete "Leger et al." and replace with -- Zhan et al. --
Item [75], Inventors, delete "James R. Leger, Plymouth, MN (US); Qiwen Zhan, Lauderdale, MN (US)" and replace with -- Qiwen Zhan, Lauderdale, MN (US); James R. Leger, Plymouth, MN (US) --.
Item [56], References Cited, OTHER PUBLICATIONS, "Chou et al." reference, delete "Chou et al.", and replace with -- Cohn et al. --.
Item [57], ABSTRACT,
Line 7, delete "Polar-", and replace with -- polar- --.

<u>Column 9,</u>
Line 40, the paragraph beginning with "Similarily," should be a continuation of the previous paragraph.

<u>Column 12,</u>
Lines 13 and 31, delete "ϕ", and replace with -- $\varphi$ --.
Line 31, delete "$e^{j\phi}$" and replace with -- $e^{j\varphi}$ --.

Signed and Sealed this

Fifteenth Day of June, 2004

JON W. DUDAS
*Acting Director of the United States Patent and Trademark Office*